United States Patent [19]

Germain

[11] 4,105,683
[45] Aug. 8, 1978

[54] METHOD OF PREPARATION OF TRIVALENT PLUTONIUM FORMIATE

[75] Inventor: Michel Germain, Marcoussis, France

[73] Assignee: Commissariat a l'Energie Atomique, Paris, France

[21] Appl. No.: 797,796

[22] Filed: May 17, 1977

[30] Foreign Application Priority Data

May 25, 1976 [FR] France .................. 76 15826

[51] Int. Cl.² .............................................. C07F 5/00
[52] U.S. Cl. .................................. 260/429.1; 423/11; 423/251
[58] Field of Search ................ 260/429.1; 423/11, 251

[56] References Cited

U.S. PATENT DOCUMENTS 3,660,047   5/1972   Grisler ........................ 260/429.1 X

OTHER PUBLICATIONS

Jezowska, B. et al.; "V(III and V(IV) Formates and their Magnetic Properties," in J. Inorg. Nucl. Chem. 31:727–731, 1969.

Crisler, L. R., J. Inorg. Nucl. Chem. 34(10):3263–3266, 1972.

Crisler, L. R., J. Inorg. Nucl. Chem. 35(12):4309–4310, 1973.

Cleveland, J. M., The Chemistry of Plutonium, Gordon & Breach Science Publishers, N.Y., 1970, p. 51.

*Primary Examiner*—Richard E. Schafer
*Attorney, Agent, or Firm*—Sidney W. Millard

[57] ABSTRACT

A nitric acid solution having a nitric acid concentration within the range of 0.01 to 15M and containing plutonium(IV) ions and/or plutonium(III) ions is reacted with a formic acid solution in order to obtain a precipitate of plutonium(III) formiate.

10 Claims, 1 Drawing Figure

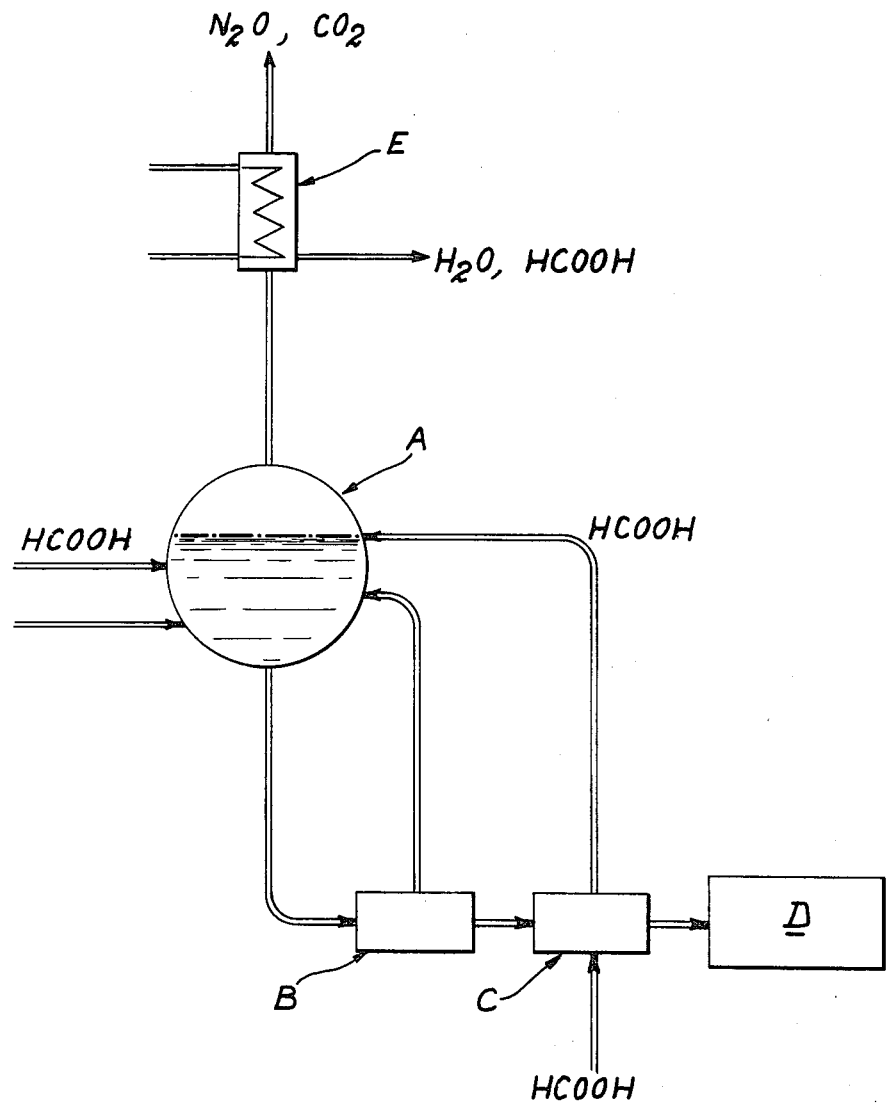

METHOD OF PREPARATION OF TRIVALENT PLUTONIUM FORMIATE

This invention relates to a method of preparation of trivalent plutonium formiate.

Trivalent plutonium formiate is an intermediate product of considerable value in the nuclear industry since it can readily be converted to plutonium dioxide by calcining in air at low temperature. Furthermore, plutonium dioxide obtained from plutonium formiate has improved properties which favor its use in many applications, especially in the fabrication of nuclear fuels.

Methods of preparation of plutonium(III) formiate which entail the use of plutonium metal as a starting product for this preparation are already known.

In accordance with these methods, the plutonium metal is first dissolved in a suitable solvent consisting for example of hydrochloric acid or a mixture of carbon tetrachloride and methanol and a precipitate of plutonium(III) formiate is then obtained from the solution thus formed by treating it with suitable reagents in a number of successive steps.

Plutonium formiate is recovered by vacuum filtration and then scrubbed once or a number of times either with methanol containing a small quantity of formic acid or with concentrated formic acid in order to remove any soluble impurities which may be present.

These methods are attended by a certain number of disadvantages which limit their development on an industrial scale. In the first place, they call for the use of plutonium metal which can be obtained only from irradiated-fuel processing solutions after many operations which are made difficult by the high radioactivity of plutonium.

In the second place, these methods call for reagents such as hydrochloric acid, carbon tetrachloride or methanol which entail difficult or hazardous use in a radioactive medium.

A final disadvantage lies in the complexity of operation since these methods involve a number of operational steps which are liable to limit the production yields of plutonium formiate.

The present invention is precisely directed to a method of preparation of plutonium(III) formiate which overcomes the various disadvantages mentioned above since it permits the precipitation of plutonium(III) formiate in a single step from nitric acid solutions containing plutonium(IV) ions and/or plutonium(III) ions such as the nitric acid solutions usually obtained in irradiated-fuel processing plants.

To this end, the method of preparation of trivalent plutonium formiate in accordance with the invention essentially consists in reacting a nitric acid solution having a nitric acid concentration within the range of 0.01 to 15M and containing plutonium(IV) ions and/or plutonium(III) ions with a formic acid solution in order to obtain a precipitate of plutonium(III) formiate.

This method takes advantage of the fact that, in a strongly acidic medium, formic acid destroys nitric acid in the hot state, reduces plutonium(IV) ions to plutonium(III) ions, reacts with plutonium(III) ions in order to form plutonium(III) formiate and that, in addition, plutonium(III) formiate is highly insoluble in a formic acid medium.

Thus, by reacting formic acid with a nitric acid solution having a nitric acid concentration within the range of 0.01 to 15M and containing plutonium(IV) nitrate or plutonium(III) nitrate, destruction of the nitric acid is obtained under the conditions of the method in accordance with the following reaction diagram:

$$2HNO_3 + 4HCOOH \rightarrow N_2O + 4CO_2 + 5H_2O \qquad (1)$$

which results in conversion of the nitric acid to water and to volatile products such as nitrous oxide and carbon dioxide gas.

The formic acid reduces the Pu(IV) nitrate which is present in the nitric acid solution to Pu(III) nitrate and reacts with the Pu(III) nitrate in accordance with the following reaction diagram:

$$Pu(NO_3)_3 + 3HCOOH \rightarrow Pu(HCOO)_3 \downarrow + 3HNO_3 \qquad (2)$$

which results in the formation of Pu(III) formiate followed by the destruction of the nitric acid in accordance with reaction (1). The two reactions can even take place simultaneously. Reaction (2) also has the effect of re-forming nitric acid and this latter is again caused to decompose by the formic acid which is present in the reaction medium. Thus in the method according to the invention, the addition of formic acid results in the production of a precipitate of trivalent plutonium formiate and the plutonium retains this valence since destruction of the nitric acid takes place in accordance with reaction (1). Since plutonium(III) formiate is highly insoluble in a formic acid medium, it is an advantage to carry out these reactions with an excess of formic acid in order to establish favorable conditions for precipitation of the plutonium formiate obtained.

In consequence, the volume ratio of the reacting solutions and their respective concentrations of plutonium, of nitric acid and of formic acid preferably have values which make it possible to obtain in the equilibrium state of the reaction a formic acid concentration of the reaction medium within the range of 5M and 20M and preferably higher than or equal to 10M.

The nitric acid solutions employed as the starting product in the method according to the invention contain plutonium in the trivalent state and/or in the tetravalent state and have a nitric acid concentration within the range of 0.01 to 15M.

In order to increase the reaction rate, it is an advantage to carry out the reaction of the solutions in the hot state and preferably at the boiling point of the mixture of said solutions, namely at a temperature of about 100° C.

The plutonium formiate obtained by means of the method in accordance with the invention can readily be converted to plutonium dioxide by calcining in air. The method in accordance with the invention therefore finds a particularly advantageous application in the preparation of plutonium dioxide.

A more complete understanding of the invention will be obtained from the following description which is given by way of example and not in any limiting sense, reference being made to the accompanying drawing which shows diagrammatically an installation for the production of plutonium formiate as contemplated in the method according to the invention.

This method consists in reacting a nitric acid solution containing plutonium(III) ions and/or plutonium(IV) ions in a reaction vessel shown at A with a formic acid solution maintained at the boiling point.

The precipitate of plutonium formate obtained as a result of this reaction is separated from the solution by filtration at B in a suitable device, for example in a vacuum. The filtered precipitate is then scrubbed with 90% formic acid at C and a purified precipitate of trivalent plutonium formate is obtained at D. The vapor and the gases evolved during the reaction are separated at E in a condensing installation into a fraction of volatile products essentially containing nitrous oxide and carbon dioxide gas which are discharged to the atmosphere and into a condensed fraction mainly containing formic acid and water, most of which is returned into the reaction vessel.

In accordance with a preferred form of the invention, precipitation of the plutonium formate is carried out continuously. In this case the nitric acid solution containing the plutonium(III) ions and/or plutonium(IV) ions and the formic acid solution are continuously fed into the reaction vessel A at the rates required for ensuring that the formic acid concentration of the reaction medium is maintained at a value within the range of 5M and 20M, taking into account the initial concentration of the solutions of nitric acid, plutonium and formic acid. The resultant mixture which contains the precipitate of plutonium formate is continuously withdrawn from the reaction vessel A, then filtered at B in a suitable filtration device. The filtrate thus obtained is recycled to the reaction vessel A and the filtered precipitate is then subjected at C to one or a number of operations which consist in scrubbing with concentrated formic acid. The formic acid employed in the scrubbing process is also recycled to the reaction vessel A and purified plutonium(III) formate is obtained at the end of the operation. Recycling of the filtrate obtained at the time of filtration of the plutonium formate precipitate makes it possible to improve the reaction efficiency, with the result that an efficiency of the order of 100% is obtained in practice. The gaseous effluents obtained by reaction of the nitric acid solution with the formic acid solution are continuously removed at the outlet of the condensing installation E and a part of the condensed liquid effluents is also continuously removed from the installation for the production of plutonium formate.

The following examples illustrate the results obtained at the time of practical application of the method according to the invention by slow introduction of a nitric acid solution containing plutonium(III) ions or plutonium(IV) ions into a formic acid solution which is brought to the boil with total reflux.

EXAMPLE 1

Into a reaction vessel having a capacity of 1000 ml containing 500 ml of 20M formic acid which were brought to the boil with total reflux, there were continuously introduced by means of a pump, at the rate of 22.5 ml per hour, 100 ml of a nitric acid solution containing 110 g/l of plutonium(IV) and having a nitric acid concentration of 5.1M. The plutonium(III) formiate was continuously formed and precipitated immediately. The final formic acid strength was 17.5M. Identification of the precipitate by thermogravimetry and by studying the spectrum of X-ray diffraction showed that the product obtained corresponded to plutonium(III) formiate having the formula:

$Pu(HCOO)_3$.

EXAMPLE 2

Into a reaction vessel having a capacity of 500 ml containing 150 ml of 15M formic acid which were brought to the boil with total reflux, there were introduced at the rate of 4.5 ml/h 15 ml of a plutonium(IV) nitrate solution containing 131.5 g/l of plutonium and having a nitric acid concentration of 4.75M. The precipitate of trivalent plutonium formate thus obtained was identified by thermogravimetric analysis.

At the end of the operation, the formic acid concentration of the reaction medium was 12.9M and the residual plutonium content of said medium was 814 mg/l.

EXAMPLE 3

Into a reaction vessel having a capacity of 500 ml containing 150 ml of 20M formic acid which were brought to the boil with total reflux, there were continuously introduced at the rate of 4.5 ml/h 15 ml of a plutonium(IV) nitrate solution containing 131.5 g/l of plutonium and having a nitric acid concentration of 4.75M.

The precipitate of trivalent plutonium formate was separated by filtration on sintered glass and identified by thermogravimetry. The formic acid concentration of the reaction medium at equilibrium was 18M and the residual solubility of the plutonium was 2510 mg/l.

EXAMPLE 4

Into a reaction vessel in a stream of nitrogen containing 30 ml of a 26M formic acid solution which was brought to the boil, there were introduced at the rate of 4.5 ml per hour 13 ml of a trivalent plutonium nitrate solution having a nitric acid strength of 1.9N and containing 61 g/l of plutonium(III) and 2 g/l of hydrazine.

The formic acid solution which was present in the vessel was previously deoxygenated by bubbling of nitrogen.

There was obtained a blue precipitate of plutonium(III) formate and, at the end of the operation, the formic acid concentration of the reaction medium was 15.2M and its residual plutonium content was 129 mg/l. The presence of nitric acid in this medium was not detected.

What we claim is:

1. A method of preparation of trivalent plutonium formate, wherein a nitric acid solution having a nitric acid concentration within the range of 0.01 to 15M and containing plutonium(III) ions and/or plutonium(IV) ions is reacted with a formic acid solution in order to obtain a precipitate of plutonium(III) formate.

2. A method according to claim 1, wherein said precipitate is scrubbed with formic acid.

3. A method according to claim 1, wherein the volume ratio of said solutions and their respective concentrations of plutonium, of nitric acid and of formic acid have values which make it possible to obtain in the equilibrium state of the reaction a formic acid concentration within the range of 5M to 20M.

4. A method according to claim 3, wherein said nitric acid solution and said formic acid solution are continuously introduced into a reaction vessel, wherein the mixture thus obtained is continuously withdrawn from said vessel and wherein said mixture is filtered in order to separate the precipitate of plutonium(III) formate and wherein the filtrate thus obtained is recycled to said reaction vessel.

5. A method according to claim 2 wherein said nitric acid solution and said formic acid solution are continuously introduced into a reaction vessel, wherein the mixture thus obtained is continuously withdrawn from said vessel and wherein said mixture is filtered in order to separate the precipitate of plutonium (III) formiate and wherein the filtrate thus obtained is recycled to said reaction vessel.

6. A method according to claim 1 wherein said nitric acid solution and said formic acid solution are continuously introduced into a reaction vessel, wherein the mixture thus obtained is continuously withdrawn from said vessel and wherein said mixture is filtered in order to separate the precipitate of plutonium(III) formiate and wherein the filtrate thus obtained is recycled to said reaction vessel.

7. A method of preparing plutonium dioxide comprising calcining the precipitate of plutonium (III) formiate of claim 1.

8. The method of claim 7 wherein said precipitate is scrubbed with formic acid prior to calcining.

9. The method of claim 7 wherein the volume ratio of said solutions and their respective concentrations of plutonium, of nitric acid and of formic acid have values which make it possible to obtain in the equilibrium state of the reaction a formic acid concentration within the range of 5M to 20M.

10. The method of claim 7 wherein said nitric acid solution and said formic acid solution are continuously introduced into a reaction vessel, wherein the mixture thus obtained is continuously withdrawn from said vessel and wherein said mixture is filtered in order to separate the precipitate of plutonium (III) formiate and wherein the filtrate thus obtained is recycled to said reaction vessel.

* * * * *